United States Patent [19]

Reger

[11] Patent Number: 5,156,610
[45] Date of Patent: * Oct. 20, 1992

[54] CATHETER ATHEROTOME

[75] Inventor: Vincent A. Reger, Portland, Oreg.

[73] Assignee: EVI Corporation, Portland, Oreg.

[*] Notice: The portion of the term of this patent subsequent to Dec. 10, 2008 has been disclaimed.

[21] Appl. No.: 800,337

[22] Filed: Nov. 26, 1991

Related U.S. Application Data

[63] Continuation of Ser. No. 660,918, Feb. 27, 1991, Pat. No. 5,071,424, which is a continuation of Ser. No. 395,500, Aug. 18, 1989, abandoned.

[51] Int. Cl.$^5$ .............................................. A61B 17/32
[52] U.S. Cl. .................................. 606/159; 606/170; 30/348
[58] Field of Search ............... 606/159, 170, 180, 167; 604/22; 128/751; 30/348, 346.6

[56] References Cited

U.S. PATENT DOCUMENTS

| | | | |
|---|---|---|---|
| 1,167,014 | 1/1916 | O'Brien . | |
| 2,505,358 | 4/1949 | Gusberg et al. | 128/2 |
| 2,541,691 | 2/1951 | Eicher | 27/24 |
| 2,655,154 | 10/1953 | Richter | 128/305 |
| 2,701,559 | 2/1955 | Cooper | 128/2 |
| 2,730,101 | 1/1956 | Hoffman | 128/305 |
| 2,816,552 | 12/1957 | Hoffman | 128/305 |
| 2,943,626 | 7/1960 | Dorima | 128/328 |
| 3,108,593 | 10/1963 | Glassman | 128/328 |
| 3,108,594 | 10/1963 | Glassman | 128/328 |
| 3,320,952 | 5/1967 | Wright | 128/173 |
| 3,320,957 | 5/1967 | Sokolik | 128/311 |
| 3,334,629 | 8/1967 | Cohn | 606/194 |
| 3,435,826 | 4/1969 | Fogarty | 128/348 |
| 3,467,101 | 9/1969 | Fogarty et al. | 128/348 |
| 3,467,102 | 9/1969 | Fogarty et al. | 128/348 |
| 3,472,230 | 10/1966 | Fogarty | 128/328 |
| 3,509,882 | 5/1970 | Blake | 128/325 |
| 3,540,431 | 11/1970 | Mobin-Uddin | 128/1 |
| 3,704,711 | 12/1972 | Park | 128/305 |
| 3,811,446 | 5/1974 | Lerwick et al. | 128/303 |
| 3,952,747 | 4/1976 | Kimmell, Jr. | 128/303 |
| 3,995,623 | 12/1976 | Blake et al. | 128/206 E |
| 3,996,938 | 12/1976 | Clark, III | 128/348 |

(List continued on next page.)

FOREIGN PATENT DOCUMENTS

| | | |
|---|---|---|
| 3532653 | 3/1987 | Fed. Rep. of Germany . |
| 8100283 | 3/1983 | PCT Int'l Appl. . |
| 197712 | 12/1977 | U.S.S.R. . |
| 764684 | 9/1980 | U.S.S.R. . |

OTHER PUBLICATIONS

Technical Features in Endarterectomy, Barry H. LeVeen, M.D. Reprint from Surgery, St. Louis, vol. 57, No. 1, pp. 22-27, 1965., from Department of Surgery, The Veterans Administration, Hospital and State University of New York, Downstate Medical Center.
Arterial Embolectomy Catheters, American Edwards Laboratories date of publication unknown.

Primary Examiner—Michael H. Thaler
Attorney, Agent, or Firm—Lynn G. Foster

[57] ABSTRACT

A catheter atherotome and method for its use for performing partial atherectomy in an artery and thereby enlarging the lumen effectively available for blood flow through the artery. Several blades are mounted at a distal end of a catheter, in a helical basket configuration and spaced angularly apart from one another about the associated ends of two concentric sheaths in such a way that longitudinal and rotary relative movement of the sheaths selectively bows the blades arcuately outwardly into a cutting position or draws the blades flat into alignment with the sheaths. The blades have sharpened cutting edges extending helically and directed toward the catheter's proximal end when the blades are bowed. Partial removal of an atheroma is effected by manually pulling the basket knife past an atheroma with the basket blades in their outwardly bowed cutting positions, with the speed, force, and amount of expansion of the blades determined by the operator. Removal of cutaway pieces of atherosclerotic plaque material is accomplished either by pull-back of a balloon embolectomy catheter or by use of a latex membrane enshrouding the spiral wire blades to trap the shavings within the membrane.

35 Claims, 3 Drawing Sheets

U.S. PATENT DOCUMENTS

| | | | |
|---|---|---|---|
| 4,020,847 | 5/1977 | Clark, III | 128/305 |
| 4,030,503 | 6/1977 | Clark, III | 128/304 |
| 4,046,150 | 9/1977 | Schwartz et al. | 128/328 |
| 4,207,874 | 6/1980 | Choy | 128/6 |
| 4,273,128 | 6/1981 | Lary | 128/305 |
| 4,290,427 | 9/1981 | Chin | 128/304 |
| 4,315,511 | 2/1982 | Chin | 128/305 |
| 4,347,846 | 9/1982 | Dormia | 128/328 |
| 4,425,908 | 1/1984 | Simon | 128/1 |
| 4,445,509 | 5/1984 | Auth | 128/305 |
| 4,452,244 | 6/1984 | Chin | 128/321 |
| 4,494,531 | 1/1985 | Gianturco | 128/1 |
| 4,559,927 | 7/1985 | Chin . | |
| 4,589,412 | 5/1968 | Kensey | 128/305 |
| 4,592,341 | 6/1986 | Omagari et al. | 128/4 |
| 4,610,662 | 9/1986 | Wiekl et al. | 604/53 |
| 4,611,594 | 9/1986 | Grayback et al. | 128/328 |
| 4,612,931 | 9/1986 | Dormia | 128/1 R |
| 4,619,246 | 10/1986 | Molgaard-Nielsen | 128/1 |
| 4,621,636 | 11/1986 | Fogarty | 128/304 |
| 4,625,726 | 12/1986 | Duthoy | 128/328 |
| 4,630,609 | 12/1986 | Chin | 128/344 |
| 4,631,052 | 12/1986 | Kensey | 604/22 |
| 4,643,184 | 2/1987 | Mobin-Uddin | 128/303 |
| 4,648,402 | 3/1987 | Santos | 128/345 |
| 4,650,466 | 3/1987 | Luther | 604/95 |
| 4,653,496 | 3/1987 | Bundy et al. | 128/305 |
| 4,655,217 | 4/1987 | Reed | 128/305 |
| 4,669,464 | 6/1987 | Sulepov | 606/200 X |
| 4,669,469 | 6/1987 | Gifford, III et al. | 128/305 |
| 4,681,106 | 0/1987 | Kensey et al. | 128/305 |
| 4,682,599 | 9/1987 | Konomura | 128/324 |
| 4,688,553 | 8/1987 | Metals | 128/1 |
| 4,692,139 | 9/1987 | Stiles | 604/22 |
| 4,696,667 | 9/1987 | Masch | 604/22 |
| 4,699,147 | 10/1987 | Chilson et al. | 128/642 |
| 4,706,671 | 11/1987 | Weinrib | 128/348.1 |
| 4,721,507 | 1/1988 | Chin | 604/100 |
| 4,723,549 | 2/1988 | Wholey et al. | 128/344 |
| 4,727,873 | 3/1988 | Mobin-Uddin | 128/303 |
| 4,732,154 | 3/1988 | Shiber | 128/305 |
| 4,739,760 | 4/1988 | Chin | 128/305 |
| 4,745,919 | 5/1988 | Bundy et al. | 128/305 |
| 4,755,175 | 7/1988 | Nilsson | 604/268 |
| 4,762,130 | 8/1988 | Fogarty | 128/348.1 |
| 4,765,332 | 8/1988 | Fischell | 128/305 |
| 4,768,505 | 9/1988 | Okada et al. | 128/328 |
| 4,768,508 | 9/1988 | Chin et al. | 128/305 |
| 4,781,177 | 11/1988 | Lebigot | 128/897 |
| 4,790,812 | 12/1988 | Hawkings, Jr. et al. | 604/22 |
| 4,793,348 | 12/1988 | Palmaz | 128/325 |
| 4,807,626 | 2/1989 | McGirr | 128/328 |
| 4,808,163 | 2/1989 | Laub | 604/105 |
| 4,819,634 | 4/1989 | Shiber | 128/305 |
| 4,820,283 | 4/1989 | Schinkling et al. | 604/280 |
| 4,820,349 | 4/1989 | Saab | 128/344 |
| 4,832,055 | 5/1989 | Palestrant | 128/899 |
| 4,842,579 | 6/1989 | Shiber | 604/22 |
| 4,850,957 | 7/1989 | Summers | 604/22 |
| 4,857,045 | 8/1989 | Rydell | 604/22 |
| 4,867,156 | 9/1989 | Stack | 128/305 |
| 4,873,978 | 10/1989 | Ginsburg | 606/198 |
| 4,886,061 | 12/1989 | Fischell et al. | 128/305 |
| 4,886,490 | 12/1989 | Shiber | 604/22 |
| 4,887,613 | 12/1989 | Farr et al. | 606/159 |
| 4,890,611 | 1/1990 | Monfort et al. | 606/159 |
| 4,892,519 | 1/1990 | Songer et al. | 604/96 |
| 4,894,051 | 1/1990 | Shiber | 604/32 |
| 4,895,166 | 1/1990 | Farr et al. | 128/751 |
| 4,895,560 | 1/1990 | Papantonakos | 604/22 |
| 4,898,575 | 2/1990 | Fischell | 604/22 |
| 4,905,689 | 3/1990 | Stack et al. | 606/3 |
| 4,909,781 | 3/1990 | Husted | 604/22 |
| 4,913,704 | 4/1990 | Kurimoto | 604/171 |
| 4,917,085 | 4/1990 | Smith | 606/159 |
| 4,917,102 | 4/1990 | Miller et al. | 128/772 |
| 4,921,478 | 5/1990 | Solano et al. | 604/53 |
| 4,921,482 | 5/1990 | Hammerslag et al. | 604/95 |
| 4,921,483 | 5/1990 | Wijay et al. | 604/96 |
| 4,921,484 | 5/1990 | Hillstead | 604/104 |
| 4,923,462 | 5/1990 | Stevens | 606/159 |
| 4,926,858 | 5/1990 | Gifford et al. | 606/159 |
| 4,943,297 | 7/1990 | Saveliev et al. | 606/200 |
| 4,957,482 | 9/1990 | Shiber | 604/22 |
| 4,966,604 | 10/1990 | Reiss | 606/159 |
| 4,986,807 | 1/1991 | Farr | 604/22 |
| 4,994,067 | 2/1991 | Summers | 606/159 |

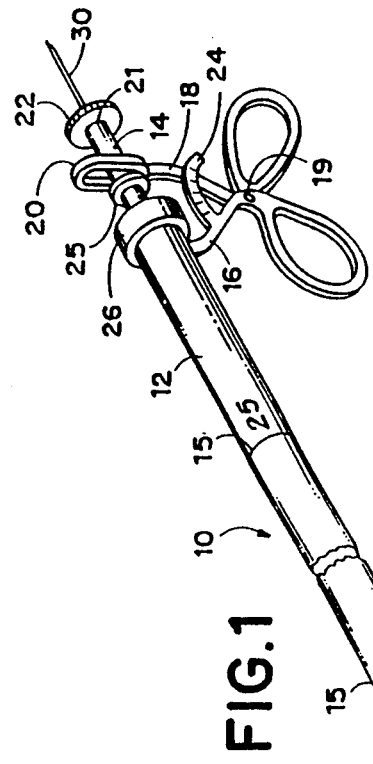
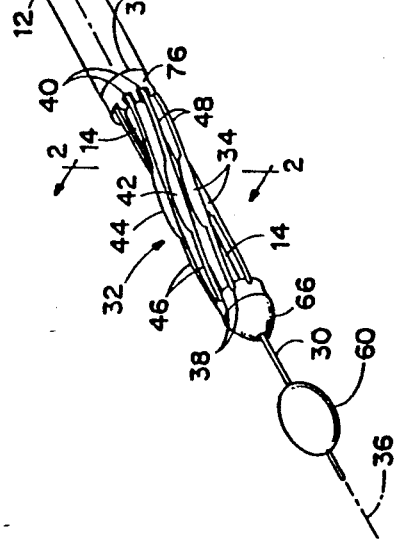
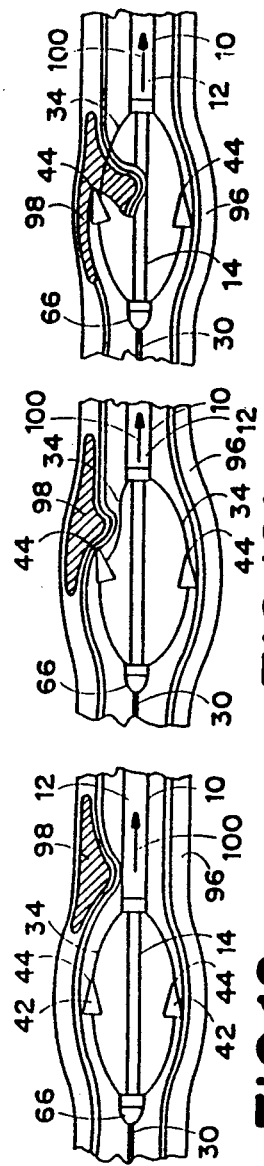
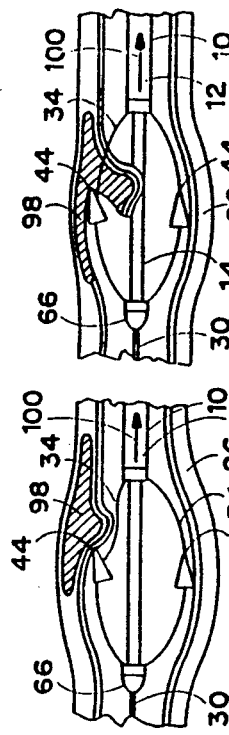
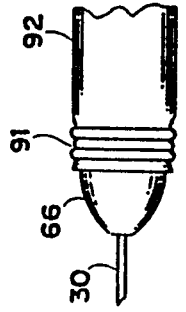
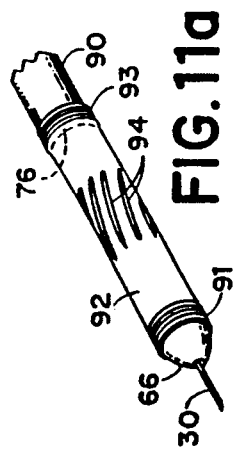

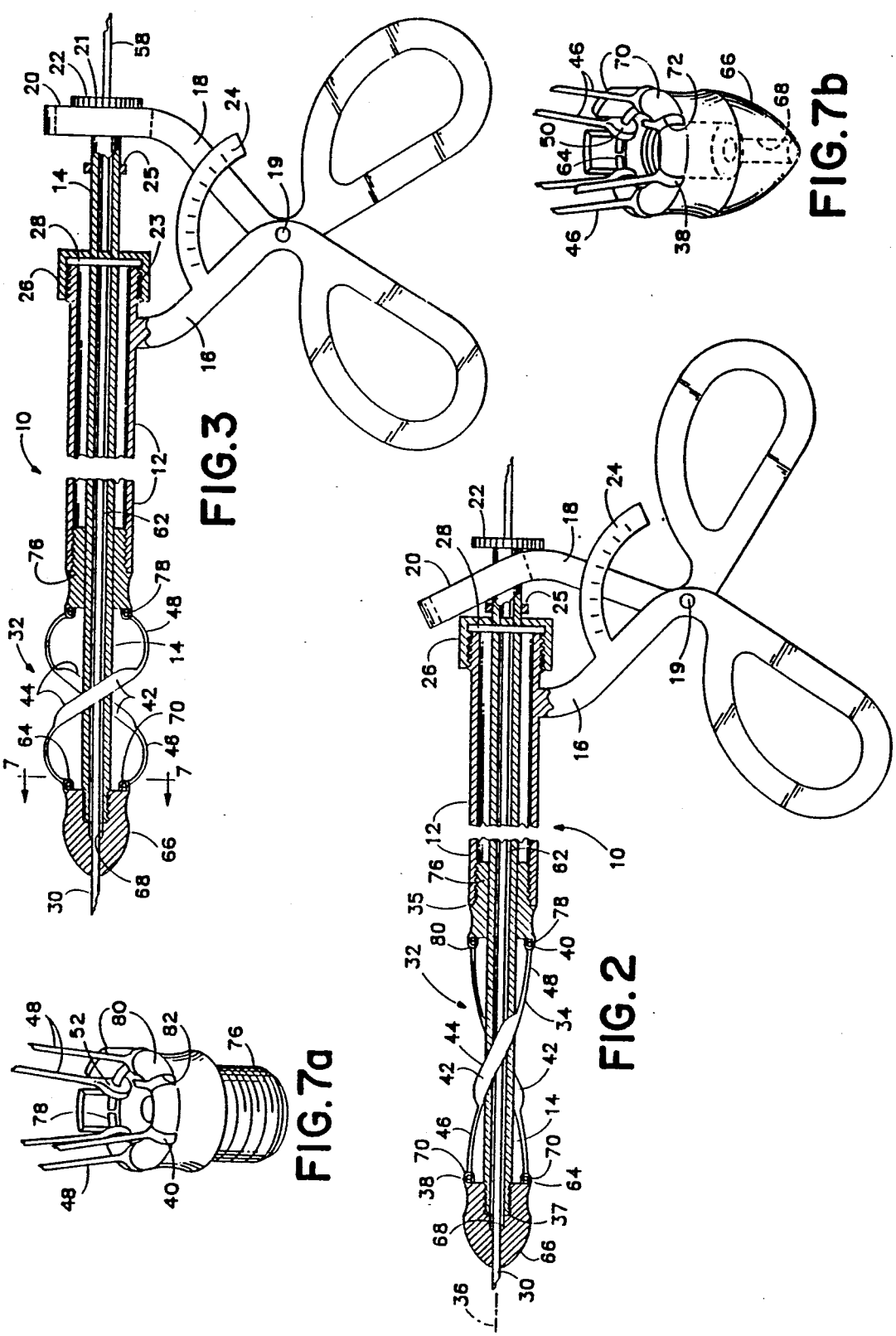

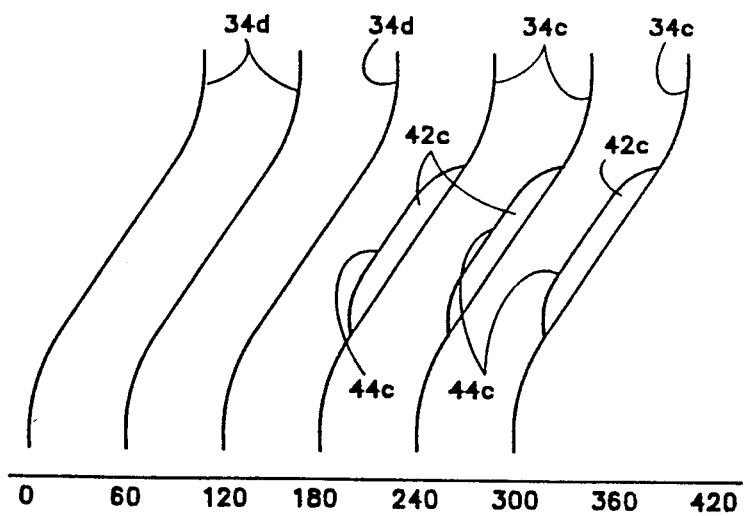
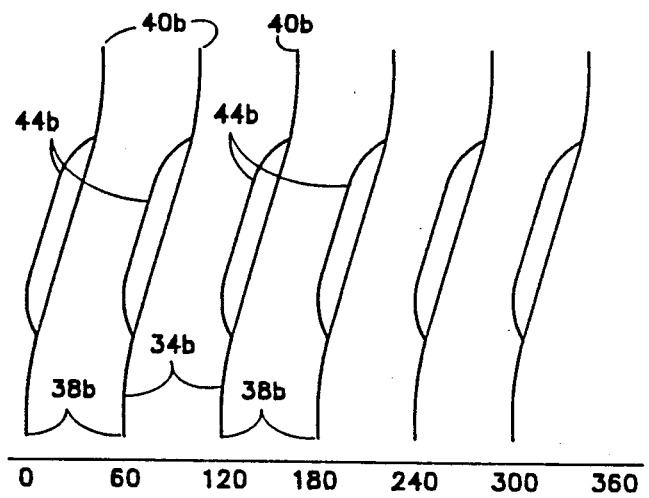
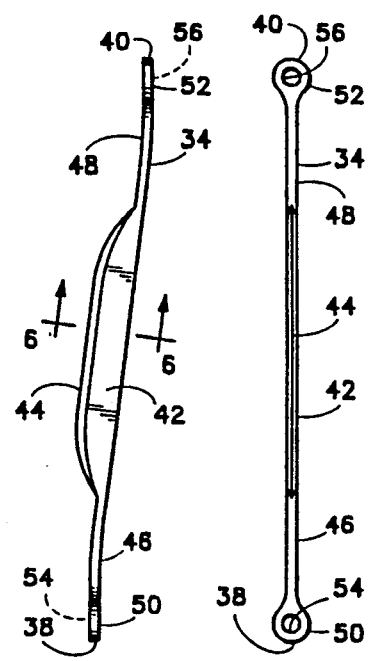
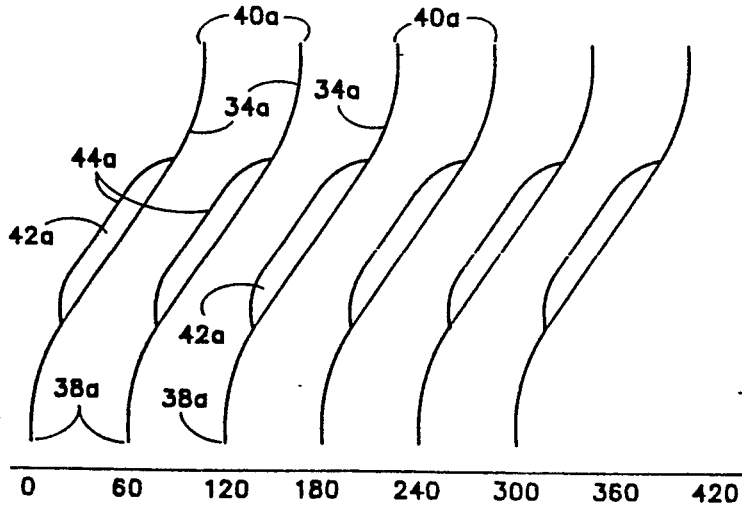
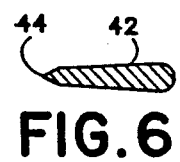

CATHETER ATHEROTOME

CONTINUITY

This application is a continuation of my copending U.S. patent application Ser. No. 660,918, filed Feb. 27, 1991, now U.S. Pat. No. 5,071,424, which is a continuation of my U.S. patent application Ser. No. 395,500, filed Aug. 18, 1989, now abandoned.

FIELD OF THE INVENTION

The present invention relates to surgical apparatus and procedures, and particularly to a device for excising portions of the atherosclerotic plaque material causing stenosis in an artery.

BACKGROUND AND RELATED ART

Atherosclerosis (Greek for soft and hard deposits) is a condition which progressively affects many arteries of the body with advancing age. It ultimately produces thickening of the medial layer of the arterial wall, which may involve some or all of the circumference of the blood vessel. Eventually, narrowed internal diameter, or stenosis, of the artery results and restricts the flow of blood to the tissue beyond the stenosis, producing symptoms including angina or myocardial infarction in the heart, claudication or gangrene in the legs, high blood pressure, or deterioration of kidney function.

The art and science involved in modern vascular surgery are comparatively young and began with the successful end-to-end repair of severed arteries in Korean war casualties. Atherosclerotic narrowing of arteries then could only be corrected by complete end-arterectomy, which required a longitudinal incision through the entire narrowed segment of an artery. Exposure of an artery for this purpose was difficult, and the wounds resulting from the surgery were large. Although results were often gratifying, the practice was not widespread because of resulting problems such as pseudoaneurysms developing in endarterized segments and the potential for vessel wall dissection at the distal endpoint, and because of the difficulty posed both for the patient and for the surgeon. During the 1950's a variety of synthetic tubular grafts were introduced and perfected for partial arterial replacement and bypasses around stenoses. Because of the relative ease of such procedures by comparison with endarterectomy, bypass grafting soon became the dominant means of correcting arterial narrowing within the pelvis and thigh. Advances in surgical technique in the late 1960's made possible the use of the patient's own reversed saphenous vein to bypass occluded arteries on the heart and below the knee.

As the population of the United States has aged as a group, the manifestations of atherosclerosis have, as a group, become this nation's number one health problem in terms of both suffering and cost. While surgical bypass procedures using saphenous vein or prosthetic conduit remain the procedure of choice in most instances, newer technologies have evolved in the last decade to simplify the treatment of atherosclerotic stenoses in an attempt to reduce patient risk, reduce cost, and to make treatment available to more people. In carefully selected cases involving narrowing of short segments of the coronary, renal, iliac, and femoral arteries balloon dilation has been employed with some success. Generally, however, the duration of arterial patency resulting from such procedures is less than for bypass graft procedures. Utilization of lasers to open narrowed arteries has not yet proven to be clinically successful and is very expensive in all aspects.

In recent years a variety of atherectomy devices have been used experimentally in attempts to extend patency. Some of these devices include rotary cutting mechanisms, which restrict their use to stenoses of short length. Some are driven by high-speed electric motors which add to their complexity and increase the likelihood of breakdown while also reducing the amount of responsiveness and taking the ability to control operation out of the surgeon's hands.

Manually-operated devices for relieving arterial stenoses are disclosed, for example, in Lary U.S. Pat. No. 4,273,128, which discloses a device having a plurality of curved knife blades whose edges are directed radially outward, and Fischell et al. U.S. Pat. No. 4,765,332, which discloses a catheter including a proximally-exposed annular cutting edge which is no greater in diameter than an outer sleeve of the catheter to which it is attached. Luther U.S. Pat. No. 4,650,466, discloses a catheter which includes an expansible woven tube portion which can be used to abrade atherosclerotic plaque from the interior wall of the artery. Clark, III, U.S. Pat. No. 4,020,847, discloses a catheter device including a slot having sharp edges extending longitudinally of the catheter to cut free dangling matter which might otherwise obstruct the lumen of an artery. Hoffman U.S. Pat. Nos. 2,730,101 and 2,816,552 disclose teat bistoury devices including blades which can be bowed outwardly along the length of each blade to protrude radially. The device is intended to be rotated to cut away restrictions in a milk canal of a cow's teat. Several prior art devices useful for manually opening venous valves are disclosed in Chin et al. U.S. Pat. Nos. 4,739,760 and 4,768,508 and Reed U.S. Pat. No. 4,655,217.

Chin U.S. Pat. No. 4,559,927 discloses an endarterectomy apparatus including a center-pull annular cutter for removing arteriosclerotic material.

Rotary, mechanically operated devices are disclosed in such patents as Sokolik U.S. Pat. No. 3,320,957, which discloses a device including an array of helical stationary blades inside which an oppositely-twisted helical rotor operates to shear material protruding inwardly between the stationary blades. Auth U.S. Pat. No. 4,445,509 discloses a fluted rotary burr. Kensey U.S. Pat. Nos. 4,589,412 and 4,631,052 disclose turbine-driven rotary devices for opening obstructed arteries, and Kensey et al. U.S. Pat. No. 4,681,106 discloses another turbine-driven rotary cutting device.

Several devices for use in retrieving stones from within bodily passageways by entrapping the stones within baskets including arrays of helical wires are disclosed in Grayhack et al. U.S. Pat. No. 4,611,594, Duthoy U.S. Pat. No. 4,625,726, Dormia U.S. Pat. Nos. 4,347,846 and 4,612,931. Related devices are disclosed by McGirr U.S. Pat. No. 4,807,626, and Hawkins, Jr. et al. U.S. Pat. No. 4,790,812, which discloses a parachute-like basket carried on a distal end of a rotatable interior member of a catheter so that the parachute-like basket can retrieve particles cut free by the interior member of the catheter. Park U.S. Pat. No. 3,704,711 discloses a device in which a radially outwardly disposed edge can be controllably concealed within a distal end of a catheter or exposed so that the blade can be used.

Balloon-tipped catheters are disclosed in Fogarty U.S. Pat. No. 3,435,826, while Fogarty U.S. Pat. No.

3,472,230 discloses a catheter including an umbrella-like skirt useful for retrieval of stones.

There still remains a need, however, for an improved atherectomy device which is simple in concept and operation, manually operable, and immediately responsive, and which is useful for all stenoses regardless of the length of the area of stenosis.

SUMMARY OF THE INVENTION

The present invention overcomes some of the shortcomings and disadvantages of the devices disclosed in the prior art by providing a catheter atherotome which is manually operable and by which a surgeon can plane away atherosclerotic plaque from within an artery by entering the artery with a catheter at a single point proximal to the plaque deposit. The plaque is cut away piecemeal, by serial pullback strokes of a basket knife carried on the distal end of the catheter and which is collapsible to a small diameter conforming to the diameter of the catheter itself. The basket knife of the catheter atherotome includes several blades which are aligned generally parallel with one another and in a generally helical arrangement about an inner portion of the catheter which extends distally beyond the distal end of an outer sheath portion of the catheter when in a retracted, relaxed configuration. Respective ends of each blade are attached to the inner member and the outer sheath of the catheter so that when the distal end of the inner member is moved closer to the distal end of the outer sheath the blade members are forced to bow outward, expanding the basket knife radially. When the blades are bowed outward, sharpened edges of the blades are exposed proximally with respect to the catheter, so that moving the catheter proximally brings the edges to bear against atherosclerotic plaque deposits to cut them away from the interior of an artery.

While it is particularly well-adapted for use in the femoral and popliteal arteries, the catheter atherotome of the invention may also be useful in the tibial and peroneal, arteries, and with entry gained via the aorta, in the heart and renal arteries.

In a preferred embodiment of the invention, both the longitudinal position and the rotational position of the inner member of the catheter are adjustable relative to the outer sheath, and the several blades are flexible, so that both the pitch and the amount of radial bowing of the blades are controllable. Preferably, the angle of attack of the sharpened edge is such that it will engage atherosclerotic plaque but not normal arterial lining tissue.

Another embodiment of the invention utilizes a more rigid basket knife in which sharpened portions of the blades overlap one another to provide complete circumferential coverage of the interior of an artery.

Yet another embodiment of the basket knife portion of the device includes cutting edges over only about half of the basket circumference, so that atherectomy can be performed on one-half of the arterial wall in locations where atherosclerosis normally involves only the posterior one-half of the artery.

Preferably, a lumen is provided in the inner member of the catheter, and a balloon-tipped catheter such as a Fogarty ® catheter is utilized to collect shavings of plaque cut free by the catheter atherotome of the invention, so that the shavings can be surgically removed through an incision in the arterial wall after atherectomy has been performed.

In another embodiment of the invention a latex skirt is provided to surround the basket knife assembly except where the cutting edges are provided, so that the shavings are trapped within the basket during each cutting pass of the basket over the plaque. This embodiment is intended for use in smaller arteries where it might be awkward or impractical to insert a balloon-tipped catheter, or where the catheter atherotome is introduced into an artery percutaneously.

In percutaneous use of the catheter atherotome of the invention a needle is inserted through the skin into an artery. A guide wire is passed through the needle bore and directed to the point of stenosis in the arterial system. The needle is removed and a dilator is passed over the guide wire and then removed, after which the catheter atherotome is inserted into the artery following the guide wire through the dilated tract into the artery and on to the point of stenosis. After appropriate excision of atherosclerotic plaque, the catheter atherotome and guide wire are removed and pressure is held at the point of skin puncture to permit closure of the artery to occur.

Objective confirmation of enlargement of the arterial lumen by the use of the catheter atherotome could be obtained either by on-the-table angiography, for comparison with the pre-operative arteriogram, or an on-the-table duplex-ultrasound measurement could be made of the arterial lumen immediately before and after use of the catheter atherotome of the present invention.

It is, therefore an important object of the present invention to provide an improved catheter atherotome for use in relief of stenoses in arteries.

It is another important object of the present invention to provide such a device which is manually adjustable between a configuration in which cutting blades are retracted and a configuration in which cutting blades are operatively positioned and exposed to a degree controllable by the user of the device.

It is an important feature of the apparatus of one embodiment of the present invention that its blades are somewhat flexible, between a position in which they move along the interior of healthy portions of an artery, and a position in which they cut away atherosclerotic plaque.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a pictorial view of a catheter atherotome which embodies the present invention, with the catheter portion shown foreshortened, and with the basket knife in a retracted or closed position.

FIG. 2 is a sectional view of the catheter atherotome shown in FIG. 1, taken along the line 2—2 of FIG. 1, and simplified by omission of some of the blades of the basket knife.

FIG. 3 is a view similar to FIG. 2, with the basket knife in an expanded, or cutting configuration.

FIG. 4 is an edge-on view of one of the blades of the basket knife of the atherotome shown in FIGS. 1–3.

FIG. 5 is a side view of the blade shown in FIG. 4.

FIG. 6 is a sectional view, taken along line 6—6 of the blade shown in FIGS. 4 and 5.

FIG. 7a is a perspective view, taken in the direction indicated generally by line 7a—7a of FIG. 1, showing a fitting for attaching the distal end of each blade to the end of the inner member of the catheter atherotome shown in FIGS. 1-3.

FIG. 7b is a perspective view, taken in the direction indicated generally by the line 7b—7b in FIG. 1, of the fitting attaching the proximal ends of the blades to the distal end of the outer sheath portion of the catheter atherotome shown in FIGS. 1-3.

FIG. 8 is a schematic view showing the arrangement of the several blades of one embodiment of the catheter atherotome of the present invention.

FIG. 9 is a view similar to that of FIG. 8, of a set of somewhat different blades for the basket knife of the catheter atherotome of FIGS. 1-3.

FIG. 10 is a view similar to that of FIG. 8, schematically showing a third set of blades which embody the invention.

FIG. 11a is a pictorial view of the basket knife portion of a catheter atherotome of an alternate embodiment of the invention, including a skirt portion associated with the blades of the basket knife.

FIG. 11b is a fragmentary side elevation view showing a detail of the embodiment of the invention shown in FIG. 11a.

FIGS. 12a, 12b, and 12c are sectional views of a portion of an artery including an atheroma, showing the action of the catheter atherotome of the present invention as it is drawn past the atheroma to remove a portion of the plaque material forming the atheroma.

DETAILED DESCRIPTION OF THE INVENTION

Referring now to the drawings which form a part of the disclosure herein, in FIGS. 1-3 a catheter atherotome 10 includes an elongate flexible tubular outer sheath 12. A similar inner member 14 of somewhat greater length is disposed within the of the outer sheath 12. The outer sheath 12 and inner member 14 are flexible enough to negotiate curves in arteries atraumatically, but are rigid enough to maintain relative position between the two, both longitudinally and rotationally. They might be made, for example, of a suitable polyvinyl chloride plastic material. Markings 15 may be provided along the outer sheath 12 to indicate the length of the catheter atherotome distal of each marking as an aid to placement in an artery.

A first lever 16 is connected with the outer sheath 12 near its proximal end. A second lever 18 is pivotally connected with the first lever 16 at a pivot joint 19. An elongate loop 20 is attached to the second lever 18 and surrounds the rear or proximal end portion 21 of the inner member 14. A stop 22 is fixedly attached to the proximal end of the inner member 14. The stop 22 is preferably larger than the loop 20 and is provided with appropriate surface configuration to permit rotation of the inner member 14 manually with respect to the outer sheath 12 by use of the stop 22. Finger loops are provided on the levers 16 and 18 for use in manipulation of the first and second levers 16 and 18 to withdraw the proximal end 21 of the inner member 14 a distance from the proximal end 23 of the outer sheath 12, as desired. A second stop 25 is preferably also located on the inner member 14, on the distal side of the loop 20, to be used, if necessary, to push the inner member 14 distally into the proximal end 23 of the outer sheath 12. Preferably, a scale 24 is provided on the first lever 16 as an indicator of the position to which the inner member 14 has been withdrawn relative to the outer sheath 12. A cap 26 is mounted on the proximal, or rear end of the outer sheath 12 by means of mating threads, and an O-ring 28, held in place by the cap 26, grips the exterior surface of the inner member 14 with an appropriately adjustable amount of force to maintain the position of the inner member 14 relative to the outer sheath 12.

The inner member 14 is tubular, with a lumen which is large enough to admit passage of a guide wire (not shown) or a balloon-tipped catheter 30 which may, for example, be a Fogarty ® arterial embolectomy catheter.

A controllably expansible basket knife 32 includes a plurality of blades 34 extending between the distal end 35 of the outer sheath 12 and the distal end 37 of the inner member 14, which extends, as previously mentioned, beyond the distal end of the outer sheath 12. While six blades, equally spaced, are shown, fewer or more might also be utilized. The catheter atherotome 10 can be of an appropriate size, depending on the size of the artery, and larger blades 34 are required for larger arteries.

As shown in FIGS. 1 and 2, when the inner member 14 is located with its distal end 37 in a position of maximum extension beyond the distal end 35 of the outer sheath 12, the blades 34 extend closely alongside the protruding portion of the inner member 14, normally in a helical configuration centered about a central longitudinal axis 36. The distal ends 38 of the several blades 34 are separated from the positions of the proximal ends 40 of the blades 34, by an angle determined by the rotational position of the inner member 14 with respect to the outer sheath 12. Thus, rotation of the inner member 14 within the outer sheath 12 causes a steeper or shallower slope or pitch of each of the blades 34. Thus, as shown in FIG. 1, the distal ends 38 of the blades are located approximately 60° offset from the respective proximal ends 40, with the blades 34 extending generally longitudinally and closely alongside the inner member 14, in a steep helix.

It should be recognized that FIGS. 2 and 3, for the sake of clarity, show but two of the blades 34, of which there would normally be a greater number, for example, six blades 34. It should further be recognized that the inner member 14 is shown in a position of rotation relative to the position of the outer sheath 12 in which the distal ends 38 are separated from the respective proximal ends 40 by about 180°. This exaggerates the degree of rotation which probably would be used in practice, in order to provide greater clarity in the figures for depiction of the effects of a combination of rotation and retraction of the inner member 14 with respect to the position of the outer sheath 12.

Referring now also to FIGS. 4, 5, and 6, it will be seen that each blade 34 includes a middle portion 42 including a sharpened edge 44, an intermediate, or strut, section 46, between the distal end 38 and the middle portion 42, and an intermediate, or strut, portion 48, located between the middle portion 42 and the proximal end 40. A pair of fins, a fin 50 proximate the distal end 38 and a parallel fin 52 proximate the proximal end 40 of the blade, respectively define bores 54 and 56. The fins 50 and 52 are oriented generally perpendicular to the orientation of a plane defined by the middle portion 42 of the blade, and the bores 54 and 56 extend generally normal to the fins 50 and 52, while the blades 34 are gently curved in an "S" shape when relaxed.

The catheter 30 extending through the catheter atherotome 10 has a balloon tip 60 which extends beyond the distal end of the catheter atherotome 10, as may be seen in FIG. 1. The catheter 30 is longer than the entire catheter atherotome 10, so that it can be manipulated at the proximal end of the catheter atherotome 10 while extending through a lumen 62 defined within the inner member 14, as shown in FIGS. 2 and 3. Such length is also desirable to provide room for cutting strokes of the atherotome with the balloon tipped catheter stationary in an artery.

The intermediate, or strut, portions 46 and 48 of each blade 34 are flexible in response to movement of the inner member 14 relative to the outer sheath 12, so that rotation of the inner member and retraction of the distal end 37 of the inner member with respect to the distal end 35 of the outer sheath result in flexure of the blades 34. Flexure takes place particularly in the strut portions 48 and 46 of the blades 34, to expand the plurality of blades 34 into a basket-like configuration in which each edge 44 is inclined more steeply with respect to the central longitudinal axis 36. While the strut portions 48 and 46 are free to bend relatively uniformly and to twist, the wider and more flattened shape of the sharpened middle portion 42 constrains its flexure to a degree which permits the edge 44 to assume an arcuate curvature centered about the inner member 14 but at a radius greater than that of the outer sheath 12, with the sharpened edge 44 directed toward the proximal end of the catheter atherotome 10. The inclination of the individual blades 34, and particularly the edge 44 thereof, is determined by both the degree to which the inner member 14 is withdrawn proximally within the distal end 35 of the outer sheath 12, and the degree of rotation of the inner member 14 with respect to the outer sheath 12. Preferably, the edge 44 can extend up to an angle of 40° to 50° relative to an imaginary equator of the basket knife 32 to achieve maximum cutting, with the equator considered to be normal to the longitudinal axis 36.

As may be seen with reference more particularly to FIGS. 7a and 7b, as well as FIGS. 2 and 3, the blades 34 are prevented from rotating with respect to the inner member 14 and outer sheath 12 by the manner in which they are attached. An articulating mounting ring 64 extends through the bores 54 of all of the several blades 34. The articulating mounting ring 64 is securely attached to a distal fitting 66, which has an ogival shape. The fitting 66 is attached to the distal end 37 of the inner member 14 by exterior threads defined on the inner member 14 and interior threads in the distal fitting 66. A bore 68 in the distal fitting 66 is an extension of the lumen 62 of the inner member 14.

The articulating mounting ring 64 is attached to the proximal end of the distal fitting 66 by a plurality of tethering hasps 70 disposed about the proximal end of the distal fitting 66 and equal in number to the number of blades 34 to be attached to the distal fitting 66. Each of the tethering hasps 70 is bent inwardly to form an arch over the articulating mounting ring. Adjacent ones of the several tethering hasps 70 cooperatively define radially extending slots 72 between one another, with the fin 50 of a respective one of the blades 34 being disposed within each of the slots 72. The slots 72 and fins 50 restrain each of the blades 34 from rotation about an axis parallel with the central longitudinal axis 36, but permit a terminal portion of each blade, including the fin 50 and the strut or intermediate portion 46, to pivot, about the articulating mounting ring 64 as the blade 34 is bowed.

A proximal blade fitting 76 is attached to the distal end 35 of the outer sheath 12 by exterior threads mated with interior threads defined in the outer sheath 12. An articulating mounting ring 78, similar to the articulating mounting ring 64, extends through the several bores 56 defined by the fins 52 of the blades 34, interconnecting all of the proximal ends 40 of the blades. The articulating mounting ring 78 is attached to the proximal fitting 76 by a plurality of tethering hasps 80 equal in number to the number of blades 34.

Similar to the tethering hasps 70, the tethering hasps 80 extend from the distal face of the proximal fitting 76 and are bent arcuately inward toward the central longitudinal axis 36 of the catheter atherotome 10, arching over and retaining the articulating mounting ring 78. The tethering hasps 80 define radially extending slots 82 between adjacent ones of the hasps 80 and restrict the proximal ends 40 of the several blades 34 from rotating about an axis parallel with the central longitudinal axis 36 of the catheter atherotome 10. Terminal portions of the blades 34 located adjacent the proximal ends 40 are free to pivot with the fins 52 rotating about the articulating mounting ring 78 in response to retraction of the distal end of the inner member 14 into the distal end of the outer sheath 12 to the position shown, for example, in FIG. 3.

Referring to FIGS. 8, 9, and 10, the configuration and degree of flexibility of a set of blades 34 may be made to provide different amounts of coverage of the circumference of the interior or lumen of an artery within which partial arterotomy is to be performed.

In FIG. 8, six blades 34a for use as part of the catheter atherotome 10 according to the present invention are shown in a simplified schematic form as if the articulating mounting rings 64 and 78 had been straightened and unwrapped from around the circumference of the inner member 14, while maintaining the circumferential spacing of the blades 34a so as to show the angular relationships between their respective opposite ends. It will be seen, then, that the angular distance of the distal ends 38a from the proximal ends 40a is greater than 60°. Thus, the distal end of one of the blades 34a is offset angularly beyond the proximal end 40 of the adjacent blade 34a, and the middle portions 42a of adjacent blades 34a also overlap one another so that the edges 44a cooperatively present a substantially continuous circular combination of cutting edges 44a to remove a layer of plaque from the entire interior surface of the atheroma being reduced on each cutting stroke of the atherotome. The blades 34a preferably are stiff enough so that the angle of incidence of the cutting edge is fairly stable, so that the cutting edge can pare off a thin slice of atherosclerotic plaque or similar material from the interior of an artery during use of the catheter atherotome 10 equipped with the blades 34a.

Referring now more particularly to FIG. 9, a set of blades 34b are shown which have less offset between the locations of their distal ends 38b and their proximal ends 40b, so that the cutting edges 44b make separate cuts which do not overlap one another ordinarily. However, the blades 34b are made with greater flexibility and less torsional rigidity than the blades 34a. This is so that, although the angle of incidence of the edges 44 ordinarily is too little to result in cutting the interior of the arterial wall, when the sharp edge 44b of an individual blade 34b "snags" on a hard irregular body of plaque the blade is everted into a cutting position with a somewhat greater angle of incidence in order to excise that piece of plaque, as will be explained more fully subsequently. Because of the lesser offset between the distal and proximal ends of the blades 34b there is an interrupted coverage of the circumference of an artery, providing space for irregular protrusions of plaque to project between the blades 34b to be engaged by the sharpened edges 44b.

In FIG. 10 is shown a set of blades 34c and 34d, of which only the three blades 34c include middle portions 42c having edges 44c, while the blades 34d have no sharpened edge portions. Thus, the set of blades 34c and 34d provide cutting edge coverage over only about one-half the interior circumference of an artery and are most useful in removing plaque from the posterior side of an artery such as the femoral artery, where atheroma normally occurs only on the posterior side of the artery. The wire blades 34d without edges then help to maintain the proper relationship between the blades 34c, and keep the basket knife apparatus centered within the arterial lumen.

In some instances a catheter atherotome may be required to be of a size that is too small to admit passage of the balloon-tipped catheter 30 therethrough. It is still necessary to be able to retrieve pieces of plaque which have been cut free from the interior wall of an artery by use of the atherotome. In order to recover the matter excised from an arterial wall, a catheter atherotome 90, shown in FIG. 11a, which is otherwise similar to the catheter atherotome 10, additionally includes a flexible tubular membrane in the form of a skirt 92 arranged about and attached to the blades 34. One end of the skirt is attached to the distal fitting 66 by means of ferrules 91 and the other end is attached to the proximal fitting 76 by means of ferrules 93. The skirt 92 is preferably adherently attached to the blades 34, at least along the middle portions 42, and slits 94 or equivalent openings are provided to expose the edges 44 and provide ingress for pieces of plaque to the interior of the skirt 92. Pieces of plaque or the like cut free from the interior wall of an artery are able to pass through the slits 94 to be collected upon retrieval of the catheter atherotome 90 from within an artery. The membrane used as the skirt 92 must be flexible and thin, yet strong and elastic enough to accommodate the adjustment of the basket knife 32. A suitable material is a thin sheet latex. The skirt 92 may be attached to distal fitting 66 and the proximal fitting 76 after assembly of the catheter atherotome 10 including the blades 34.

Referring now to FIGS. 12a, 12b, and 12c, showing a portion of an artery 96 including an atheroma 98, the catheter atherotome 10 is illustrated schematically to show its use. As shown in FIG. 12a, the catheter atherotome 10 has been inserted into the artery from right to left. Thereafter, the inner member 14 has been withdrawn a distance into the distal end 35 of the outer sheath 12, so that the blades 34 are bowed, to place the middle portion 42 of each blade at an increased radial distance away from the inner member 14 and to cause the sharpened edges 44 to come into proper position.

To excise a portion of the atheroma 98, the catheter atherotome is manually pulled to the right as shown in FIG. 12b, and as indicated by the arrow 100. As the inwardly projecting atheroma 98 is encountered by the upper blade 34, and particularly by the edge 44, engagement of the edge 44 in the atheroma plaque material causes the edge 44 to be everted into a cutting position in which it digs into the plaque material and begins to cut a portion of the plaque material free, as may be seen in FIG. 12c. Torsional forces developed in the strut portions 46 and 48 control the angle of incidence of the edge 44, allowing the middle portion 42 to be moved to such a cutting position when plaque is encountered. However, where there is no plaque material present, as in the lower portions of the artery shown in FIGS. 12a, 12b, and 12c, the edge 44 of the respective blade 34 is oriented so that it does not catch the intima of the arterial wall and simply slides along the interior wall of the artery without doing any cutting.

The surgeon using the catheter atherotome 10 can repeatedly move the basket knife 32 back and forth in the area of an atheroma such as the atheroma 98, cutting away a thin layer of plaque with each pass in the direction indicated by the arrow 100 in FIGS. 12b and 12c, until the lumen of the artery 96 has been opened sufficiently. After each cutting stroke the entire catheter atherotome 10 will be rotated through an angle which can be determined by the position of the levers 16 and 18, so as to result in excision of plaque in an evenly distributed pattern about the interior of the artery. Thereafter, the inner member 14 may be allowed to resume its extended position beyond the distal end of the outer sheath 12, using the loop 20 (see FIG. 1) against the second stop 25 if necessary, thus retracting the middle sections 42 of the blades 34 closer to the inner member 14. The catheter atherotome 10 can then be withdrawn from the artery, followed by withdrawal of the balloon-tipped catheter 30, with the balloon 60 (see FIG. 1) inflated to retrieve the material which has been cut free from the arterial wall during the process.

The procedure is similar when using the catheter atherotome 90 (FIG. 11), except that the material cut free from the arterial wall would be retained within the membrane skirt 92 for retrieval along with the atherotome 90 when it is withdrawn from the artery.

The catheter atherotome 10 may be introduced into an artery including a stenosis by providing access to the artery and opening the arterial wall at a position more proximal to the heart than the location of the stenosis. Preferably, a guide wire is introduced into the artery and past the stenosis. Thereafter, if required, a dilator may be introduced into the artery, guided by the wire. The dilator may then be withdrawn and the catheter atherotome 10 according to the present invention may be inserted into the artery along the guide wire, which may then be withdrawn and replaced by the balloon-tipped catheter 30. After inflation of the balloon 60 to prevent loss of pieces of material cut free from the arterial wall by the atherotome 10, the basket knife 32 may be expanded to the required size by withdrawal of the inner member 14 into the distal end 35 of the outer member 12 a required distance by squeezing together the finger loops of the levers 16 and 18, so that the elongate loop 20 acts upon the stop 22 to withdraw the proximal end 21 of the inner member 14 at the proximal end of the catheter atherotome 10. Preferably, the scale 24 provided on the lever arm 16 may be used to determine when the inner member 14 has been withdrawn sufficiently to provide the required expansion of the basket knife 32.

Thereupon, the catheter atherotome may be withdrawn past the location of the atheroma, with the sharpened edges 44 of the blades 34 of the basket knife 32 paring away a portion of the plaque from the interior of the artery. The atherotome is then pushed into the artery until the blades 34 are beyond the atheroma, and rotated to a desired position for a subsequent pull-back cutting stroke. After several strokes, for example, six to ten cutting strokes, sufficient enlargement of the lumen of the artery should have taken place, and the basket blade 32 can be relaxed, contracting the blades 34 into position alongside the inner member 14 as shown in FIG. 1, so that the atherotome can be withdrawn from the artery.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. An elongate blade for use in a catheter atherotome basket knife which selectively surgically pares away atherosclerotic plaque from an interior lumen of an artery only when the basket knife is drawn proximally across a site comprising the plaque, said elongate blade comprising:

means for interconnecting each end of the elongate blade to a knife forming fitting;

means centrally disposed along the length of the elongate blade for surgically paring the plaque from the interior lumen of the artery comprising a sharpened plaque planing edge only along the side of the paring means to be proximally disposed in the knife fitting;

in combination, means to be proximally and distally disposed in the basket knife between the surgically paring means and the interconnecting means for radially bowing the blade outwardly when the interconnecting means are moved closer one to the other or when the relative radial position of said interconnecting means is appropriately changed, the radially bowing means comprising structure which is more flexible than the surgically paring means and therefore being principally responsible for bowing the elongate blade to form a circumferentially extended planing portion of the basket knife and for varying angles of incidence and attack of the surgically paring means while the radius of curvature of the surgical paring means relative to a longitudinal axis of the catheter remains relatively unchanged.

2. The elongate blade according to claim 1 wherein the surgically paring means comprise a blunt, non-cutting margin along the side opposite the side comprising the plaque planing edge.

3. The elongate blade according to claim 1 wherein the bowing and angle varying means to be proximally disposed in the basket knife comprise a portion which responsively everts the surgically paring means upon contact with proximally disposed plaque to change the angle of attack such that the plaque planing edge more effectively pares the plaque.

4. The elongate blade according to claim 1 wherein the interconnecting means comprise means for hingeably affixing each end of the elongate blade to the knife forming fitting.

5. The elongate blade according to claim 4 wherein the affixing means comprise fin shaped fittings disposed normally to a plane of the surgically paring means.

6. The elongate blade according to claim 5 wherein each fin shaped fitting comprises a hole for connecting to an articulating ring in the knife forming fitting.

7. The elongate blade according to claim 1 wherein the surgically paring means comprise means for attaching a means for trapping accumulating material planed from the interior lumen of the artery.

8. The elongate blade according to claim 1 further generally comprising an "S" shape.

9. An elongate blade for use in a catheter atherotome basket knife which selectively surgically pares away atherosclerotic plaque from an interior lumen of an artery only when the basket knife is drawn proximally across a site comprising the plaque, said elongate blade comprising:

means for interconnecting each end of the elongate blade to a knife forming fitting;

means centrally disposed along the length of the elongate blade for surgically paring the plaque from the interior lumen of the artery comprising a sharpened plaque planing knife-edge only along a side to be proximally disposed in the knife fitting;

in combination, means to be proximally and distally disposed in the basket knife between the surgically paring means and the interconnecting means for radially bowing the blade outwardly when the interconnecting means are moved closer one to the other or when the relative radial position of said interconnecting means is appropriately changed, the radially bowing means comprising structure which is more flexible than the surgically paring means and therefore being principally responsible for bowing the elongate blade to form a circumferentially extended planing portion of the basket knife and for varying angles of incidence and attack of the surgically paring means while the radius of curvature of the surgical paring means relative to a longitudinal axis of the catheter remains relatively unchanged; the bowing and varying means comprising a segment which everts the surgically paring means responsive to contact with irregular plaque surfaces proximally disposed to the basket knife in the arterial lumen and thereby changes the angles of incidence and attack of the plaque planing knife-edge to cut more effectively.

10. A catheter atherotome basket knife which selectively surgically pares away atherosclerotic plaque from an interior lumen of an artery only when the basket knife is drawn proximally across a site comprising the plaque, said basket knife comprising:

at least two elongate blades;

a first knife forming end fitting comprising means for securely attaching one end of the basket knife to a distal end of a first elongated member of a catheter atherotome;

a second knife forming end fitting comprising means for securely attaching an opposing end of the basket knife to a second elongated member of the catheter atherotome which is translationally and rotationally movable relative to the first elongated member;

the first knife forming end fitting comprising means for affixing one end of each of the elongate blades thereat;

the second knife forming end fitting comprising means for affixing the other end of each of the elongate blades thereat such that the angular separation of the ends of each of the elongate blades is substantially the same;

each of the elongate blades comprising:

means for interconnecting each end of each elongate blade to a predetermined knife forming end fitting;

means centrally disposed along the length of the elongate blade for surgically paring the plaque from the interior lumen of the artery, the paring means comprising a sharpened plaque planing knife-edge only along the side of the surgically paring means proximally disposed in the basket knife;

in combination, flexible means disposed proximally and distally in the basket knife between the surgically paring means and the interconnecting means for bowing the elongate blade to form an outwardly extended planing portion of the basket knife and for varying angles of incidence and attack of the surgically paring means responsive to translational and rotational movement of the elongate members of the catheter atherotome.

11. The basket knife according to claim 10 wherein the proximally disposed bowing and angle varying means comprise a segment which everts the surgically paring means responsive to contact with irregular plaque surfaces in the arterial lumen and thereby effectively changes the angles of incidence and attack of the surgically planing means.

12. The basket knife according to claim 10 wherein the interconnecting means comprise means for affixing each end of the elongate blade to the knife forming fitting.

13. The basket knife according to claim 12 wherein the affixing means comprise fin shaped fittings disposed normally to a plane of the paring means.

14. The basket knife according to claim 13 wherein each fin shaped fitting comprises a hole for connecting to an articulating ring in the knife forming fitting.

15. The basket knife according to claim 10 wherein each of the surgically paring means comprise means for attaching means for trapping accumulating material planed from the interior lumen of the artery.

16. The basket knife according to claim 10 wherein the surgically paring means are less flexible than the interconnecting means.

17. A catheter atherotome basket knife which selectively surgically pares away atherosclerotic plaque from an interior lumen of an artery only when the basket knife is drawn proximally across a site comprising the plaque, said basket knife comprising:

at least two elongate blades;

a first knife forming end fitting comprising means for securely attaching one end of the basket knife to a distal end of a first elongated member of a catheter atherotome;

a second knife forming end fitting comprising means for securely attaching an opposing end of the basket knife to a distal end of a second elongated member of the catheter atherotome which is translationally and rotationally movable relative to the first elongated member;

the first knife forming end fitting comprising means for affixing a predetermined end of each of the elongate blades thereat;

the second knife forming end fitting comprising means for affixing the other end of each of the elongate blades thereat;

each of the elongate blades comprising:

means for interconnecting each end of the elongate blade to the knife forming fitting;

means centrally disposed along the length of the elongate blade for surgically paring the plaque from the interior lumen of the artery, the paring means comprising a sharpened plaque planing edge only along the side of the surgically paring means which is proximally disposed in the basket knife;

in combination, flexible means proximally and distally disposed between the surgically paring means and the interconnecting means for bowing the elongate blade to form an outwardly extended planing portion of the basket knife and for varying angles of incidence and attack of the surgically paring means responsive to translational and rotational movement of the elongated members of the catheter atherotome;

the proximally disposed flexible bowing and angle varying means comprising a segment which everts the surgically paring means responsive to contact with irregular plaque surfaces in the arterial lumen and thereby effectively changes the angles of incidence and attack of the plaque planing edge.

18. A catheter atherotome which is sufficiently flexible to follow a path of an artery in which the atherotome is insertably guided and is used in surgical removal of plaque from an interior wall site of the artery, said catheter atherotome comprising:

an elongate flexible tubular outer sheath having respective proximal and distal ends;

an elongate flexible tubular inner member disposed within and translationally and rotationally movable relative to said outer sheath and having proximal and distal ends;

a basket knife having a predetermined proximal and distal orientation involving a basket knife proximal end and a basket knife distal end, means for attaching one basket knife end at the distal end of the outer sheath and means for attaching the other basket knife end at the distal end of the inner member such that the basket knife proximal end is proximally disposed;

the basket knife comprising a plurality of elongate blades each longate blade comprising flexible intermediate portions having a predetermined proximal and distal orientation associated with the orientation of the basket knife and attached to the basket knife such that, when the distal end of the outer sheath and the distal end of the inner member are disposed closer to each other, the elongate blades flex into a radially outwardly bowed arcuate configuration and, when the distal end of the outer sheath and the distal end of the inner member are moved to remove the flex of the elongate blades from the radially outwardly bowed arcuate configuration, the basket knife assumes a collapsed structure having substantially the same axial diameter as the catheter at the proximal end of the basket knife.

at least some of the elongate blades defining a respective medially disposed knife-like sharpened edge oriented on the elongate blade such that when the elongate blades flex into a radially outwardly bowed arcuate configuration, each knife-like sharpened edge is proximally disposed so as to cuttingly engage plaque associated with an inner wall of an artery as said catheter atherotome is moved within said artery in a proximal direction.

19. The catheter atherotome according to claim 18 wherein said inner member defines lumen means for receiving a guide wire extending through said inner member for guiding said catheter atherotome within said artery.

20. The catheter atherotome according to claim 18 comprising means for moving said inner member relative to said outer sheath.

21. The catheter atherotome according to claim 20 wherein said moving means comprise lever operated means for moving said inner member relative to the outer sheath.

22. The catheter atherotome according to claim 21 wherein said lever operated means comprise means for providing a scale readout of the relative distance of separation between the distal ends of the inner member and outer sheath.

23. The catheter atherotome according to claim 18 wherein at least one of such elongate blades is free of sharp edges.

24. The catheter atherotome according to claim 23 wherein the basket knife comprises at least one elongate blade comprising a sharp edge juxtaposed at least one elongate blade free of sharp edges.

25. The catheter atherotome according to claim 18 wherein the basket knife comprises each at least one elongate blade comprising a sharp edge juxtaposed an elongate blade free of sharp edges.

26. The catheter atherotome according to claim 18 further comprising means for rotating the outer sheath relative to the inner member and thereby rotating one end of the basket knife relative to the other end.

27. The catheter atherotome according to claim 18 further comprising means for rotating the inner member relative to the outer sheath and thereby rotating one end of the basket knife relative to the other end.

28. The catheter atherotome according to claim 18 wherein the basket knife comprises an array of said elongate blades disposed in a cutting position with said sharp edges exposed toward said proximal end of said outer sheath and extending generally circumferentially about said catheter when said distal end of the outer sheath and the distal end of the inner member are contracted toward each other and said bowed members are in said bowed condition.

29. The catheter atherotome according to claim 18 wherein said inner member is tubular and further including balloon-tipped catheter means, disposed within and extending through said inner member and having an inflatable balloon tip located distally beyond said distal end of said inner member and elongate blades, for retraining and retrieving pieces of material cut free from an atheroma during use of said catheter atherotome.

30. The catheter atherotome according to claim 18 further comprising skirt means of flexible membranous material arranged about said elongate blades for retrieving pieces of material pared from an artery.

31. The catheter atherotome according to claim 18 wherein the basket knife comprises a plurality of elongate blades helically oriented to define a basket equator.

32. The catheter atherotome according to claim 31 wherein the plurality of helically oriented elongate blades numbers six.

33. The catheter atherotome according to claim 18 wherein said intermediate portions comprise flexible and twistable segments and each said knife-like edge is normally oriented helically about a central longitudinal axis of the catheter and defining angles of incidence and attack, said angle of incidence being proximal and said angle of attack being shallow enough so that said knife-like sharpened edge ordinarily will not cuttingly engage the surface of the interior tissue of a healthy artery but great enough so that said knife-like sharpened edge will cuttingly engage atherosclerotic plaque projecting from the interior surface of the artery, said intermediate portions being torsionally elastic enough to permit said middle portions of said elongate blades to rotate resiliently to a position in which said knife-like sharpened edges can engage and pare away a portion of said plaque material from said interior surfaces of said artery.

34. The catheter atherotome according to claim 18 wherein each elongated blade comprises a blunt distally disposed back margin permitting the basket knife to be moved distally without cutting independent of the radially outward bowed configuration of the elongate blades.

35. The catheter atherotome according to claim 18 further comprising means for rotating the inner member relative to the outer sheath to change an angle of the proximal end of the basket knife relative to the distal end of the basket knife and thereby torsionally change the angle of attack of each sharpened knife-like edge.

* * * * *